US006417180B1

(12) United States Patent
Brown et al.

(10) Patent No.: US 6,417,180 B1
(45) Date of Patent: Jul. 9, 2002

(54) ZINC FINGER-REACTIVE ANTIMICROBIAL COMPOUNDS

(75) Inventors: Neal C. Brown, Northboro; Marjorie H. Barnes, Shrewsbury; George E. Wright, Worcester, all of MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 09/168,180

(22) Filed: Oct. 7, 1998

(51) Int. Cl.$^7$ .................... C07D 519/00; C07D 417/06; A61K 31/501; A61K 31/522; A61P 31/04
(52) U.S. Cl. .................. 514/183; 514/211.11; 514/261; 514/262; 514/272; 514/274; 540/468; 540/552; 544/276; 544/277; 544/312; 544/321
(58) Field of Search ........................... 514/183, 211.11, 514/261, 266, 272, 274, 262; 540/468, 552; 544/265, 277, 311, 320, 276, 312, 321

(56) References Cited

U.S. PATENT DOCUMENTS

| | | | |
|---|---|---|---|
| 5,516,905 A | 5/1996 | Brown et al. | 544/312 |
| 5,837,808 A | * 11/1998 | Ku et al. | 530/324 |
| 6,028,170 A | * 2/2000 | Ku et al. | 530/324 |
| 6,046,228 A | * 4/2000 | Rice et al. | 514/441 |

FOREIGN PATENT DOCUMENTS

| | | | |
|---|---|---|---|
| EP | 447324 | * | 9/1991 |
| WO | 9606614 A1 | * | 3/1996 |

OTHER PUBLICATIONS

Cristalli, G. et al, Drug Devel. Research, 45, 1998, 176–181.*
Goldner, H. et al, Ann. 691, 1966, 142–158; cited in Chemical Abstracts, vol. 64, No. 13, Jun. 20, 1996, abstract 19611c..*
Friesen, W.J et al, J. Biol. Chem., Oct. 30, 2000.*
Rice, W.G. et al, Science, 270 (5239) 1995, 1194–1197, abstract only.*
Maynard et al, Proc. Natl. Acad. Sci., 95, 1998, 11578–11583.*
Rice et al, Antimicrobial Agents and Therapeutics, 41, 1997, 419–426.*
Klug, "Zinc Finger Peptides . . . ," J. Mol. Biol., 293:215–218, 1999.
Kim, "Getting a handhold . . . ," Proc. Natl. Acad. Sci., 95:2812–2817, 1998.
Barnes et al., "DNA polymerase III of *Mycoplasma pulmonis*: isolation and characterization of the enzyme and its structural gene, polC, Molecular Microbiology," 13(5), 843–854 (1994).
Braithwaite et al., "Compilation, alignment, and phylogenetic relationships of DNA polymerases," Nucleic Acids Research, vol. 21, No. 4, pp. 787–802, 1993.
Brown et al., "Rational Design of Bubstrate Analogues Targeted to Selectively Inhibit Replication–Specific DNA Polymerases," Drugs Expt Clin. Res. XII(6/7), pp. 555–564 (1986).
Fujita et al., "Metal–Chelating Inhibitors of a Zinc Finger HIV–EP1. Rembarkable Potentiation of Inhibitory Activity by Introduction of SH Groups," J. Med. Chem, 39:503–507, 1996.
Hammond et al., "*Bacillus subtilis* DNA polymerase III: complete sequence, overexpression, and characterization of the polC gene," Gene, 98, pp. 29–36 (1991).
Jaffe et al., "Porphobilinogen Synthase Modification with Methylmethanethiosulfonate," The Journal of Biological Chemistry, vol. 259, No. 8, pp. 5032–5036 (1984).
Loo et al., "Biophysical Characterization of Zinc Ejection from HIV Nucleocapsid Protein by Anti–HIV 2.2–Dithiobis [benzamides] and Benzisothiazolones," J. Med. Chem., 39:4313–4320 (1996).
Louie et al., "A cobalt complex that selectively disrupts the structure and function of zinc fingers," Proc. Natl. Acad. Sci. USA vol. 95, pp. 6663–6668, Jun. 1998.
Low et al., Purification and Characterization of DNA Polymerase III from *Bacillus subtilis*, The Journal of Biological Chemistry, vol. 251, No. 5, Issue of Mar. 10, pp. 1311–1325, 1976.
Otsuka et al., "Novel Zinc Chelators Which Inhibit the Binding of HIV–EP1 (HIV Enhance Binding Protein) to NF–κB Recognition Sequence," Med. Chem, 37:4267–4269, 1994.
Pacitti et al., "Characterization and overexpression of the gene encoding *Staphylococcus aureus* DNA polymerase III," Gene, 165 (1995) 51–56.
Rice et al., "Evaluation of Selected Chemotypes in Coupled Cellular and Molecular Target–Based Screens Identifies Novel HIV–1 Zinc Finger Inhibitors," J. Med. Chem, 3606–3616, 1996.
Rice et al., Virus–encoded Zinc Fingers as Target for Antiviral Chemotherapy, Medical Virology, vol. 6, 187–199 (1996).
Woese et al., "Phylogenetic analysis of the mycoplasmas," Proc. Natl. Acad. Sci, vol. 77, pp. 494–498 (1980).

* cited by examiner

*Primary Examiner*—Richard L. Raymond
*Assistant Examiner*—Thomas McKenzie
(74) *Attorney, Agent, or Firm*—Fish & Richardson P.C.

(57) ABSTRACT

The invention relates to antimicrobial compounds which interact with zinc in a zinc finger of a bacterial DNA polymerase, methods of screening for such compounds, and methods of using such compounds to inhibit polymerase activity or bacterial growth.

19 Claims, No Drawings

ZINC FINGER-REACTIVE ANTIMICROBIAL COMPOUNDS

STATEMENT AS TO FEDERALLY SPONSORED RESEARCH

This invention was made with a Government grant from the National Institutes of Health (GM45330). The Government may have certain rights in the invention.

FIELD OF THE INVENTION

The invention relates to DNA polymerases and antimicrobial compounds.

BACKGROUND OF THE INVENTION

Gram-positive eubacteria include a number of human pathogens, including Staphylococcus aureus, responsible for many human nosocomial soft-tissue infections. Like other common eubacteria, Gram-positive eubacteria absolutely require DNA polymerase III for their growth and replication.

Discovered in 1972, eubacterial DNA polymerase III (pol III) is the major polymerase enzyme involved in DNA replication and is therefore essential for cell division. Two classes of pol IIIs are known.

The Gram-positive pol IIIs are so-named because they were first discovered in the Gram-positive eubacterium Bacillus subtilis. Later it was recognized that Gram-positive pol IIIs are encoded by the polC gene. The polC gene product is generally a polypeptide which is about 1430–1460 amino acids in length, and which integrates both an 3'-5' exonuclease site and a polymerase site. The Gram-positive pol IIIs are uniquely sensitive to inhibitory dGTP analogs of the so-called "HPUra" type (Brown, *Proc. Natl. Acad. Sci. USA*, 67:1454, 1970).

Gram-negative pol IIIs are so-named because they were first discovered in the Gram-negative bacterium *Escherichia coli*. The Gram-negative pol IIIs are encoded by the dnaE gene, are typically 1155–1165 amino acids in length, contain only the polymerase site, and are completely insensitive to HPUra-like compounds.

The genomes of Gram-negative eubacteria apparently contain dnaE but not polC. The genomes of Gram-positive eubacteria and mycoplasmas contain both polC and dnaE. The dnaE gene product is required for replication of the Gram-negative bacterial genome, while the polC gene product is required for replication of the Gram-positive and mycoplasmal bacterial genomes. The function of the dnaE gene product in Gram-positive bacteria and mycoplasma is unclear.

SUMMARY OF THE INVENTION

The invention is based on the discovery that the DNA polymerase III of Gram-positive eubacteria and mycoplasmas contain a zinc finger domain adjacent to the polymerase active site, and that the integrity of the zinc finger is required for polymerase activity.

Accordingly, the invention features methods of identifying compounds that inhibit infections by Gram-positive eubacteria and mycoplasmas and the new antimicrobial compounds themselves.

In general, the invention features a compound for inhibiting Gram-positive eubacterial or mycoplasmal infection. The compound includes a zinc finger-reactive moiety, a linker, and a Gram-positive eubacterial or mycoplasmal DNA polymerase III active site-binding moiety connected to the zinc finger-reactive moiety via the linker. The compound can have the formula:

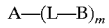

where B is a zinc finger-reactive moiety, L is a linker, and A is a polymerase III active site-binding moiety. Examples of A include:

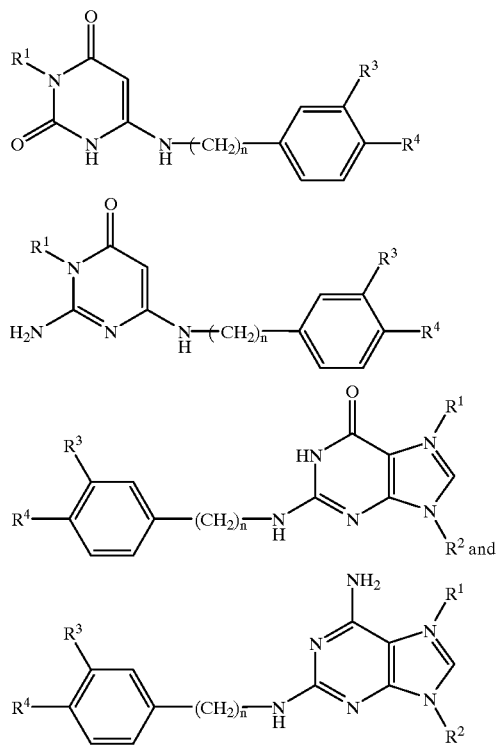

in which each of $R^1$ and $R^2$, independently, is hydrogen, $C_{1-3}$ alkyl, $C_{1-3}$ haloalkyl, or —L—B; each of $R^3$ and $R^4$, independently, is hydrogen, $C_{1-3}$ alkyl, halo, $C_{1-3}$ haloalkyl, or —L—B; m is 1 or 2; and n is 0, 1, or 2; provided that at least one of $R^1$, $R^2$, $R^3$, and $R^4$, is —L—B. The invention also includes salts of the compounds of the invention. L can be a direct bond or a $C_{1-18}$ alkylene chain. The alkylene chain optionally containing 1 to 5 ether groups, thioether groups, amine groups, ester groups, thioester groups, or amide groups. B can contain an azodi(bis)urea group, an aromatic or aliphatic disulfide group, an aromatic or aliphatic nitroso group, a thiosulfonate group, or a thiazolidone group.

Examples of B include:

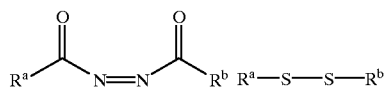

-continued

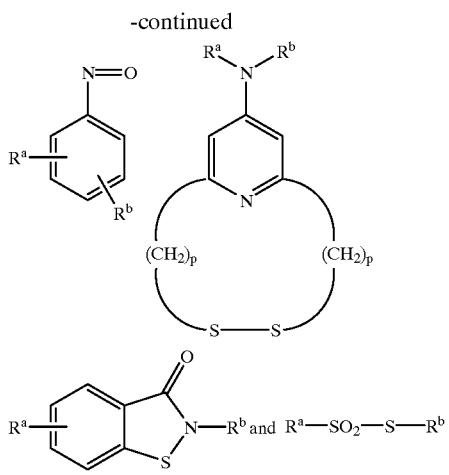

where each of $R^a$ and $R^b$, independently, is hydrogen, $C_{1-6}$ alkyl, phenyl, $C_{1-6}$ hydroxyalkyl, $C_{1-6}$ haloalkyl, amine, or —L—A; and p is 1, 2, 3, or 4; provided that either one of $R^a$ and $R^b$ is —L—A, and $R^a$ and $R^b$ are not —L—A simultaneously. The invention also includes a salt of any of the above compounds.

In another aspect, the invention includes a method of inhibiting the polymerase activity of a zinc finger-containing DNA polymerase (e.g., a Gram-positive eubacterial DNA polymerase III or a mycoplasmal DNA polymerase III, such as the *Bacillus subtilis* DNA polymerase III) by contacting the DNA polymerase with a compound (e.g., a compound of the invention) under conditions sufficient for the compound to remove or interacts with a zinc ion bound to a zinc finger in the DNA polymerase.

The invention also includes a method of decreasing the rate of cell division of a bacterium containing a zinc finger-containing DNA polymerase (e.g., a Gram-positive eubacterial DNA polymerase III or a mycoplasmal DNA polymerase III, such as the *Bacillus subtilis* DNA polymerase III) by exposing the bacterium to a compound (e.g., a compound of the invention) under conditions sufficient for the compound to enter the bacterium and interact with a zinc ion bound to a zinc finger in the DNA polymerase.

In yet another aspect, the invention includes a method for testing whether a compound decreases the rate of cell division of a bacterium (e.g., a Gram-positive eubacterium or a mycoplasma) containing a zinc finger-containing DNA polymerase by exposing a bacterium containing a zinc finger-containing DNA polymerase to the compound under conditions sufficient for the compound to enter the bacterium; and determining whether a zinc ion (e.g., a $^{65}Zn$ ion) is bound to a zinc finger of the DNA polymerase, where binding of a zinc ion to the zinc finger in the absence of the compound but not in the presence of the compound indicates that the compound decreases the rate of cell division of the bacterium. The zinc finger-containing DNA polymerase can be at least 70% homologous or identical to SEQ ID NO:1 and comprises the sequence:

Z—$X_2$—Cys—$X_{15-27}$—Cys—$X_2$—Cys (SEQ ID NO:5)

where Z is His or, Cys, $X_2$ is any two consecutive amino acids, and $X_{15-27}$ is any 15 to 27 consecutive amino acids. For example, the zinc finger-containing DNA polymerase can include SEQ ID NO:2. In other embodiments, the zinc finger-containing DNA polymerase comprises the sequence:

CyS—$X_2$—Cys—$X_{19-21}$—Cys—$X_2$—Cys (SEQ ID NO:6)

where $X_2$ is any two consecutive amino acids, and $X_{19-21}$ is any 19 to 21 consecutive amino acids.

The invention also includes a method for testing whether a compound inhibits a zinc finger-containing DNA polymerase by providing a mixture that includes a polypeptide including a zinc finger of a zinc finger-containing DNA polymerase; mixing the compound with the mixture under conditions sufficient to allow the compound to contact the zinc finger; and determining whether a zinc ion is bound to the zinc finger, where binding of the zinc ion to the zinc finger in the absence of the compound but not in the presence of the compound indicates that the compound inhibits the DNA polymerase. In some embodiments, the mixture includes a cell containing the polypeptide.

In a different aspect, the invention includes a method of determining whether a compound inhibits a zinc finger-containing DNA polymerase by providing a mixture that includes a bacterium containing a zinc finger-containing DNA polymerase; mixing the compound with the mixture under conditions sufficient to allow the compound to contact the DNA polymerase within the bacterium, the compound including a group that interacts with zinc in a zinc finger; and measuring polymerase activity of the DNA polymerase in the presence of the compound, where a polymerase activity in the presence of the compound less than the polymerase activity in the absence of the compound indicates that the compound inhibits the DNA polymerase.

In still another aspect, the invention includes a method of treating a mammal susceptible to or having an undesirable Gram-positive eubacterial or mycoplasmal infection by administering to the mammal an amount of a compound (e.g., a compound of the invention) sufficient to interact with zinc in a zinc finger-containing DNA polymerase within a bacterium such that the polymerase activity of the DNA polymerase is inhibited. This method of the invention is especially useful in treating a mammal susceptible to or having an undesirable Gram-positive eubacterial infection.

The invention also includes polypeptides useful in the methods of the invention that include a zinc finger of the sequence $CX_2CX_{19-21}CX_2C$ (SEQ ID NO:6) or $HX_2CX_{21-24}CX_2C$ (SEQ ID NO:7), where C is cysteine, H is histidine, $X_2$ is any two consecutive amino acids, $X_{19-21}$ is any 19 to 21 consecutive amino acids, and $X_{21-24}$ is any 21 to 24 consecutive amino acids, and can optionally include a polymerase domain. The polypeptides of the invention are shorter than any naturally occurring Gram-positive eubacterial or mycoplasmal pol III.

The new antimicrobial compounds or agents can exist as neutral compounds or salts. For example, the amine groups can be positively charged and form a salt with anions, e.g., bromide. Likewise, any anionic groups of the antimicrobial agent can form a salt with an cation, e.g., a sodium ion, a potassium ion, or an ammonium ion.

Typical alkyl groups are, e.g., methyl, ethyl, propyl, isopropyl, butyl, isobutyl, hexyl, heptyl, octyl, and dodecyl. An alkylene chain is a bivalent alkyl radical.

Halo groups are halogen radicals, e.g., chloro, bromo, or iodo. The halo group in a haloalkyl can attach to any carbon atom of the alkyl group. Likewise, the hydroxy group in a hydroxyalkyl can also attach to any carbon atom of that alkyl group.

When an ester group, a thioester group, or an amide group is present in a new antimicrobial compound, these groups can be connected in either orientation. For example, an ester group can be present as —C(═O)—O— or —O—C(═O)—.

The nitrogen atom of an amine or an amide can be bonded to a hydrogen or a $C_{1-3}$ alkyl group.

A "zinc finger" is a polypeptide sequence that specifically binds zinc by coordination with (1) four Cys residues, (2) three Cys residues and one His residue, or (3) two Cys residues and two His residues within the polypeptide sequence.

A "zinc finger-reactive moiety" is a compound or a portion of a compound which, upon contacting a zinc finger, removes the zinc ion from the zinc finger or otherwise interacts with the zinc ion to change the three-dimensional structure of the zinc finger so that an enzymatic activity of a polypeptide containing the zinc finger, e.g., the polymerase activity of pol III, is inhibited.

A "DNA polymerase" is a protein or polypeptide that catalyses the polymerization of 2'-deoxyribonucleoside-5'-triphosphates., By "inhibiting" or "inhibited" is meant partial or complete inhibition.

A "bacterium" is a eubacterium or a member of the order Mycoplasmatales, e.g., a species of the genus Mycoplasma, Spiroplasma, Ureaplasma, or Acholeplasma.

To determine the "percent identity" of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions× 100).

The "percent homology" between two sequences can be determined using a mathematical algorithm. A preferred, non-limiting example of a mathematical algorithm utilized for the comparison of two sequences is the algorithm of Karlin et al., *Proc. Natl. Acad. Sci. USA*, 87:2264–2268 (1990), modified as in Karlin et al., *Proc. Natl. Acad. Sci. USA*, 90:5873–5877 (1993). Such an algorithm is incorporated into the NBLAST and XBLAST programs of Altschul et al., *J. Mol. Biol.*, 215:403–410 (1990). BLAST nucleotide searches can be performed with the NBLAST program, score=100, wordlength=12 to obtain nucleotide sequences homologous to T139 nucleic acid molecules of the invention. BLAST protein searches can be performed with the XBLAST program, score=50, wordlength=3 to obtain amino acid sequences homologous to T139 protein molecules of the invention. To obtain gapped alignments for comparison purposes, Gapped BLAST can be utilized as described in Altschul et al., *Nucleic Acids Res.*, 25:3389–3402 (1997). When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers et al., *CABIOS* (1989). Such an algorithm is incorporated into the ALIGN program (version 2.0) which is part of the GCG sequence alignment,software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Among other advantages, the methods of the invention provide a mode of intervention for antibacterial agents which was not previously recognized, namely, antibacterial agents based on the ability to remove or otherwise interact with a zinc ion from a zinc finger within a polypeptide. In addition, the compounds of the invention provide tight specificity for Gram-positive eubacteria and mycoplasmas by combining DNA polymerase III active site-specific chemical groups and zinc finger-reactive chemical groups. Moreover, the present invention provides antimicrobial agents that should be effective against multiple drug resistant (MDR) bacteria, because of their unique and irreversible inhibition of pol III.

Other features and advantages of the invention will be apparent from the following detailed description, and from the claims.

DETAILED DESCRIPTION

The invention relates to the finding that a unique zinc finger in Gram-positive eubacterial and mycoplasmal DNA polymerase III can be used as a drug target for new antimicrobial compounds. Since disruption of the zinc finger irreversibly inhibits polymerase activity, and such activity is essential for bacterial growth, compounds that specifically disrupt the zinc finger form a new and distinct class of antimicrobial agents. These antimicrobial agents can be used to formulate pharmaceutical compositions suitable for treating mammals (e.g., humans, dogs, cats, horses, cows, and pigs) at risk for or already infected with a Gram-positive eubacterium or mycoplasma. The recognition of the importance of the zinc finger for polymerase activity, and therefore for Gram-positive eubacterial or mycoplasmal growth, also leads to new methods of screening for potential antimicrobial compounds.

I. Discovery of a Zinc Finger in Eubacterial DNA Polymerase III and Mycoplasmal DNA Polymerase A) Production and Isolation of DNA Polymerase The polC-specific DNA polymerases useful in the methods of the invention include any naturally occurring Gram-positive eubacterial or mycoplasmal DNA polymerase III. In addition, the invention includes the use of polypeptides having additions or substitutions of amino acid residues within a naturally occurring Gram-positive eubacterial or mycoplasmal pol III. To facilitate production of Gram-positive eubacterial pol III polypeptides, nucleic acids containing the whole or a part of a polC sequence encoding such a pol III can be used for expression. For example, a nucleic acid sequence encoding the Bacillus subtilis pol III is available as GenBank Accession No. X52116. The sequence encodes the following pol III amino acid sequence:
MEQLSVNRRQFQILLQQINMTDDTFMTY-
FEHGEIKKLTIHKASKSWHFHFQFKSLL- PFQIYDTLTTRLTQSFAHIAKVTSSIEVQDAEVSESIV-
DYWSRCIEELQGISPPIISLLNQQKPKLKGNKLIVK-
TKTDTEAAALKNKYSSMIQAEYRQFGFPDLQLDA-
EIFVSEQEVQKFREQKLAEDQERAMQALIEMEKKD-
KESDEDQAPSGPLVIGYQIKDNEEIRTLDSIMDEERR-
ITVQGYVFDVETRELKSGRTLCIFKITDYTNSILIKM-
FAREKEDAALMKSLKKGMWVKARGSIQNDTFVRD-
LVMIANDVNEIKAKTREDSAPEGEKRVELHLHSPMS-
QMDAVTGIGKLVEQAK KWGHEAIALTDHAVVQS-
FPDAYSAAKKHGIKMIYGMEANLVDDGVPIAYNA-
AHRLLEEETYVVFDVETTGLSAVYDTIIELAAVKV-
KGGEIIDKFEAFANPHRPLSATIIELTGITDDMLQD-
APDVVDVIRDFREWIGDDILVAHNASFDMGFLNVA-
YKKLLEVEKAKNPVIDTLELGRFLYPEFKNHRLNT-
LCKKFDIELTQHHRAIYDTEATAYLLLKMLKDAA-
EKGIQYHDELNENMGQSNAYQRSRPYHATLLAV-
NSTGLKNLFKLVSLSHIHYFYRVPRIPRSQLEKYRE-
GLLIGSACDRGEVFEGMMQKSPEEVEDIASFYDY-
LEVQPPEVYRHLLELELVRDEKALKEIIANITKLGE-
KLNKPVVATGNVHYLNDEDKIYRKILISSQGGAN-
PLNRHELPKVHFRTTDEMLEAFSFLGEEKAKEIVV-
TNTQKVASLVDDIKPIKDDLYTPKIEGADEEIREM-
SYQRARSIYGEELPEIVEARIEKELKSI-
IGHGFAVIYLISHKLVKRSLDDGYLVG-
SRGSVGSSLVATLTEITEVNPLPP
<u>HYVCPECQHSEFFNDGSVGSGFDLPDKTCPHC</u>GT-
PLKKDGHDIPFETFLGFKGDKVPDIDLNFSGEYQP-
QAHNYTKVLFGEDNVYRAGTIGTVAEKTAYGYV-
KGYAGDNNLHMRGAEIDRLVQGCTGVKRTTGQ-
HPGGIIVVPDYMDIYDFSPIQFPADATGSEWKTTH-
FDFHSIHDNLLKLDILGHDDPTVIRMLQDLSGIDP-
KTIPTDDPEVMKIFQGTESLGVTEEQIGCKTGTLG-
IPEFGTRFVRQMLEDTKPTTFSELVQISGLSHGTDV-
WLGNAQELIHNNICELSEVIGCRDDIMVYLIYQGL-
EPSLAFKIMEFVRKGKGLTPEWEEEM-
NNVPDWYIDSCKKIKYMFPKAHAAAYVLMAVRIA-
YFKVHHALLYYAAYFTVRADDFDIDTMIKGSTAIR-
AVMEDINAKGLDASPKEKNLLTVLELALEMCERG-
YSFQKVDLYRSSATEFIIDGNSLIPPFNSIPGLGTNA-
ALNIVKAREEGEFLSKEDLQKRGKVSK-
TILEYLDRHGCLESLPDQNQLSLF (SEQ ID NO:1)
In the above sequence, the proposed zinc finger amino acid sequence (underlined) is HYVCPECQHSEFFNDGSVGS-GFDLPDKTCPHC (SEQ ID NO:2). Twenty four amino acids C-terminal to this sequence is the conserved amino acid sequence PDID (bold) (SEQ ID NO:3). Thus, it appears that the zinc finger is part of the polymerase active site.

Nucleic acid sequences encoding mycoplasmal pol IIIs are also available. For example, the *M. pulmonis* DNA polymerase sequence is described in the GenBank profile of Accession No. U06833.

In general, the DNA polymerases can be isolated from their natural bacterial sources using standard techniques. Alternatively, the DNA polymerases can be produced by transformation (transfection, transduction, or infection) of a host cell with a DNA polymerase encoding DNA fragment in a suitable expression vehicle. Suitable expression vehicles include plasmids, viral particles, and phage. For insect cells, baculovirus expression vectors are suitable. The entire expression vehicle, or a part thereof, can be integrated into the host cell genome. In some circumstances, it is desirable to employ an inducible expression vector, e.g., the LAC-SWITCH™ Inducible Expression System (Stratagene; LaJolla, Calif.).

Those skilled in the field of molecular biology will understand that any of a wide variety of expression systems can be used to provide the recombinant protein. The precise host cell used is not critical to the invention.

Preferred DNA polymerases are those which are soluble under normal physiological conditions. Also within the invention are fusion proteins in which a portion (e.g., the zinc finger) of a DNA polymerase is fused to an unrelated protein or polypeptide (i.e., a fusion partner) to create a fusion protein. The fusion partner can be a moiety selected to facilitate purification, detection, or solubilization, or to provide some other function. Fusion proteins are generally produced by expressing a hybrid gene in which a nucleotide sequence encoding all or a portion of DNA polymerase is joined in-frame to a nucleotide sequence encoding the fusion partner. For example, the expression vector pUR278 (Ruther et al., *EMBO J.*, 2:1791, 1983), can be used to create lacZ fusion proteins. The pGEX vectors can be used to express foreign polypeptides as fusion proteins containing glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

A fusion protein can be readily purified by an antibody specific for the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers. The same procedure can be used for a bacterial culture.

Alternatively, a DNA polymerase or a portion thereof, can be fused to an immunoglobulin Fc domain. Such a fusion protein can be readily purified using an affinity column.

Both naturally occurring and recombinant forms of DNA polymerases can be isolated to be used in the methods of the invention. Secreted forms can be isolated from culture media, while non-secreted forms can be isolated from the host cells. Further purification can be accomplished by affinity chromatography. In one example, a hexahistidine-tagged derivative of *B. subtilis* pol III (produced as described herein) is expressed in *E. coli*. The bacteria is lysed, and the lysate is passed through a Ni-charged IMAC-agarose column (Sigma), which is prepared according to manufacturer's instructions. The recombinant polymerase is then eluted using an imidazole gradient. Fractions are collected and assayed for polymerase activity. Active fractions are pooled to obtain a mixture containing the polymerase.

Once isolated, the DNA polymerase can, if desired, be further purified and/or concentrated, as long as further processing does not impair the polymerase activity, which can be measured using the procedures described herein. A variety of methods for purification and concentration are well known in the art (see, e.g., Fisher, *Laboratory Techniques In Biochemistry And Molecular Biology*, eds., Work and Burdon, Elsevier 1980), including ultracentrifugation and/or precipitation (e.g., with ammonium sulfate), microfiltration (e.g., via 0.45 µm cellulose acetate filters), ultrafiltration (e.g., with the use of a sizing membrane and recirculation filtration), gel filtration (e.g., columns filled with Sepharose CL-6B, CL-4B, CL-2B, 6B, 4B or 2B, Sephacryl S-400 or S-300, Superose 6 or Ultrogel A2, A4, or A6; all available from Pharmacia), fast protein liquid chromatography (FPLC), and high performance liquid chromatography (HPLC).

B) Determining the Zinc Content of a DNA Polymerase

The zinc content of a DNA polymerase can be determined by methods well known to those skilled in the art of biochemistry. For example, a DNA polymerase produced and isolated by any of the methods described above can be dialyzed in an aqueous solution containing EDTA for a length of time sufficient to scavenge non-specifically bound zinc. It is known that a zinc ion bound to a zinc finger cannot be easily removed with EDTA (Klug et al., *FASEB J.*, 9:597–604, 1995). Standard procedures for preparing a metalloprotein for analysis, including one that contains a zinc finger, are described in Vallee et al., *Physiol. Rev.*, 73:79–118 (1993). Such procedures includes segregation of glassware for use in metalloprotein analysis from other laboratory glassware. Such glassware should be washed only with distilled, deionized water. An isolated DNA polymerase is then subjected to atomic absorption spectroscopy to determine the zinc content.

C. Finding the Zinc Finger

A DNA polymerase that is found to contain a zinc ion may contain a zinc finger. Zinc fingers are extremely diverse in sequence, requiring the presence of only four amino acid residues for coordination of the zinc ion in a stretch of at least 10 consecutive amino acids. The four amino acids are four cysteines, three cysteines and one histidine, or two cysteines and two histidines. Zinc fingers are further described in Klug et al., supra. Although a wide variety of proteins contain a zinc finger, no DNA polymerase, other than the Gram-positive eubacterial DNA pol III, has been definitively found to contain this structure.

It has been found that Gram-positive eubacterial and mycoplasmal pol III contain a zinc finger. The zinc finger sequences among these bacteria are highly homologous and correspond to either a $CX_2CX_{19-21}CX_2C$ (SEQ ID NO:6) or a $HX_2CX_{21-24}CX_2C$ (SEQ ID NO:7) zinc finger structure, where the X represents any amino acid and the subscript represents the number of consecutive amino acids. A DNA polymerase useful in the methods of the invention includes the general sequence formula: $ZX_2CX_{15-27}CX_2C$ (SEQ ID NO:5) or $ZX_2CX_{18-24}CX_2C$ (SEQ ID NO:8) where Z is Cys or His. Examples within this general formula are $CX_2CX_{19-21}CX_2C$ (SEQ ID NO:6) and $HX_2CX_{21-24}CX_2C$ (SEQ ID NO:7).

As an initial evaluation, the amino acid sequence of the DNA polymerase can be aligned with previously described zinc finger sequences (see, e.g., Braithwaite et al., supra) or with the zinc finger sequences described herein. If significant homology between the polymerase sequence and a known zinc finger sequence is found and the critical four amino acids are identified within the context of the generic sequences described herein, then site-directed mutagenesis can be used to mutate any of the critical amino acids to, for example, alanine. If the polymerase zinc finger is authentic and critical to the function of the enzyme, then replacement of any of the critical amino acids should affect the polymerase activity of the enzyme.

Validating that a functional (i.e., required for polymerase activity) zinc finger exists in an essential DNA polymerase of a pathogenic organism provides a new drug target for inhibiting the growth of that organism.

II. General Methodology for Disrupting a Zinc Finger in a DNA Polymerase

A) Zinc Finger-Reactive Moieties

By identifying a functional zinc finger in a DNA polymerase, one skilled in the art can inhibit the polymerase by changing the structure of the zinc finger (e.g., by ejecting zinc), thereby inhibiting the growth of an organism that relies on the DNA polymerase for replication. Changes in zinc finger structure can be induced by contacting the zinc finger with a compound that is known to react or interact with a zinc finger. Alternatively, the compound is not initially known to alter zinc finger structure but rather is selected from a library of compounds screened against a zinc finger of the present invention for this;activity. Such compounds are well known in the art, including those described in Rice et al., *J. Med. Chem.*, 39:3606–3616 (1996); Otsuka et al., *J. Med. Chem.*, 37:4267–4269 (1994); Otsuka et al., *J. Med. Chem.*, 38:3264–3270 (1995); Fujita et al., *J. Med. Chem.*, 39:503–507 (1996); Loo et al., *J. Med. Chem.*, 39:4313–4320 (1996); Jaffe et al., *J. Biol. Chem.*, 259:5032–5036 (1984); and Louie et al., *Proc. Natl. Acad. Sci. USA*, 95:6663–6668 (1998). A more detailed discussion of zinc ejectors appears below.

B) Targeting a Zinc Finger-Reactive Moiety to the DNA Polymerase Active Site

To increase the specificity of zinc finger-reactive moieties for Gram-positive eubacterial or mycoplasmal pol III, any of the zinc finger-reactive moieties described herein can be linked, e.g., covalently linked, to a compound known to bind to the polymerase active site of those DNA polymerases (e.g., the HPUra-like compounds disclosed in U.S. Pat. No. 5,516,905). A zinc finger-reactive moiety brought to such close proximity to the zinc finger via an active site-binding component is expected to increase specificity or potency of the antimicrobial compounds of the invention.

For example, HPUra-like compounds are a class of uracil-based microbial agents that specifically target Gram-positive eubacterial and mycoplasmal DNA pol III by binding to a portion of the polymerase active site. This portion is less than 24 amino acids away from the C-terminus of the zinc finger domains identified herein, and so is in close spatial proximity to the zinc finger.

Thus, by linking a HPUra-like compound to a compound known to react with a zinc finger., a new class of antimicrobial agents specific for Gram-positive eubacteria and mycoplasma are produced. Further details on the synthesis of these new antimicrobials are given below.

III. Screening for Candidate Antimicrobial Compounds

The recognition that an authentic zinc finger is presented in Gram-positive eubacterial and mycoplasmal pol III forms a basis for a new class of antimicrobials against these microorganisms. Thus, candidate compounds (e.g., compounds from a chemical library) can be initially screened for antimicrobial activity by using relatively inexpensive and microarrayable zinc binding or ejection as a surrogate activity. Several screening procedures are described below.

A) Measuring Zinc Released from a DNA Polymerase

A candidate antimicrobial can be tested for its ability to eject zinc from a DNA polymerase by a variety of methods. For example, a bacterium producing a DNA polymerase useful in the methods of the invention can be grown in media free of environmental zinc and supplemented with radioactive $^{65}Zn$.

The zinc-free media can be prepared by first mixing a sufficient amount of Chelex-Na (Bio-Rad) into the media for a time sufficient to remove environmental zinc. The Chelex is removed from the media, and $[^{65}Zn]Cl_2$ is added to the media to about 0.5 to 2 µCi/ml media. The bacteria are then grown in this labeling media, and the radioactive zinc-labeled DNA polymerase is isolated and purified using the methods described above. Preferably, zinc which is non-specifically bound to the DNA polymerase is removed by the dialyzation process described above.

The candidate antimicrobial compound can be added to an aqueous mixture or solution of the isolated, zinc-labeled DNA polymerase under conditions that allow contact between the zinc finger of the polymerase and the compound. For ease of measurement, the polymerase is optionally attached to a solid support, e.g., a Sepharose bead. If the compound is effective in ejecting zinc from the zinc finger, radioactivity is released into the solution and lost from the protein. Either the radioactivity level of the protein or the radioactivity of the protein-free solution can be counted by standard methods to determine if the compound is effective. The compound is considered effective in ejecting zinc if at least 25% of the specifically bound zinc is removed by the compound. Preferably at least 50% (e.g., at least 75%, 90%, or 95%) of the zinc is removed.

B) Measuring Polymerase and Exonuclease Activities

After passing the initial screen, a candidate antimicrobial can also be screened for its ability to inhibit a DNA polymerase activity. The effect of the compound on exonuclease activity, as well as polymerase activity, can be measured.

Polymerase activity can be measured by any number of methods well known in the art, e.g., the method described in Barnes et al., *Meth. Enzymol.*, 262:35–42 (1995). Briefly, five microliters of an appropriate dilution of enzyme is rapidly mixed with 20 µl of polymerase assay mix (18.75 mM Tris [pH 7.5], 12.5 mM magnesium acetate, 31.25 µm DATP, 31.25 µm dCTP, 31.25 µm dGTP, 12.5 µm [methyl-$^3$H]dTTP [1.5 µCi/µmol], 1.25 mM DTT, 20% glycerol, and 0.5 mg/ml activated DNA), and incubated at 30° C. for 10 minutes. Reactions are stopped by addition of 0.5 ml cold 10% trichloroacetic acid (TCA) in 10 mM sodium pyrophosphate. After approximately 10 minutes at 0° C., samples are filtered on Whatman GF/A filters and washed, first with cold 1 M HCl in 100 mM sodium pyrophosphate, then with cold ethanol. Filters are dried and their radioactivity quantitated by liquid scintillation counting.

For determination of the Michaelis constant ($K_M$) of the polymerase for DNA, the concentration of activated calf thymus DNA is varied during the assay from 0.0 to 0.8 mg/ml. For determination of the $K_M$ for dGTP, incorporation of [$^3$H]dTMP can be followed as a function of dGTP concentration (e.g., from 0.0 to 0.5 mM), and the values for incorporation are corrected for dGTP-independent background incorporation.

Exonuclease activity also can be measured by methods well known in the art, including those described in Barnes et al., supra. For example, five microliters of an appropriate dilution of enzyme is quickly mixed with 45 µl of exonuclease assay mix (33.3 mM Tris [pH 7.5], 7.4 mM magnesium chloride, 3.3 mM DTT, 11.1% glycerol, and $^3$H-labeled denatured DNA [0.05–0.2 µg/µl; about 70,000 cpm/assay]), and incubated at 30° C. for 10 minutes. Reactions are stopped by addition of 0.5 ml 10% TCA in 10 mM sodium pyrophosphate. Fifty microliters of a 10 mg/ml solution of bovine serum albumin is added as a coprecipitant. After about 10 minutes at 0° C., samples are centrifuged at 15,000 g for 20 minutes. Then 400 µl of the supernatant is removed and assayed for radioactivity in 2 ml of an aqueous scintillant. If the presence of the compound in the reaction leads to a substantial decrease in the exonuclease activity, the candidate compound is effective in inhibiting exonuclease activity.

For determination of the $K_M$ for the exonuclease substrate, the concentration of single-stranded DNA is varied from 0.0 to 0.2 mg/ml.

C) Measuring Bacteriocidal Activity

A candidate antimicrobial compound can be screened for its ability to decrease the rate of cell division of a bacterium (bacteriostatic and/or bacteriocidal activity). Methods of measuring the rate of cell division are well known in the art. For example, the rate of cell division can be measured by counting the difference in cell number at two time points, taking the $\log_2$ of that difference, and dividing that value by the time elapsed between the two time points. If the measured rate of cell division of a bacterium grown in the presence of the compound is substantially less than in the absence of the compound, the candidate compound is effective in decreasing the rate of cell division.

As an example of a primary screen, the candidate antimicrobial compound is dissolved in sterile DMSO and diluted 100-fold (final DMSO concentration of 1%) into Mueller-Hinton broth (MHB; Difco) containing log-phase methicillin-sensitive *S. aureus* (ATCC No. 29213) at about $10^6$ colony forming units (cfu) per milliliter. The control culture contains only 1% DMSO. Compound and control cultures are incubated at 37° C., and samples from the cultures are removed at specific times during the next 24 hours. Each sample is assayed for bacteria in cfu/ml by diluting in MHB and plating on LB agar plates. The candidate compound is said to have bacteriocidal activity if the cfu/ml of the relevant sample is reduced by at least 50% in the presence of:the compound as compared to in the absence of the compound.

To determine if any of the compound-exposed bacteria has developed resistance to the antimicrobial compound, bacteria are grown for three days in medium containing a concentration of the compound which still allows at least some growth. This;bacteria is used in a secondary bacteriocidal activity assay (same procedure as above). Resistance is indicated if the decrease in cfu/ml seen in the secondary assay is substantially less than the decrease in cfu/ml seen in the primary assay. Alternatively, $10^8$ cfu of bacteria is plated on 150 mm petri plates containing 3×, 10×, or 30× MIC of the antimicrobial compound. After incubation at 37° C. for three days, colonies are counted and related to the number of cells plated to give an estimate of the mutation frequency.

D) Minimal Inhibitory Concentration (MIC)

To determine minimal inhibitory concentration of a candidate antimicrobial compound, log-phase bacterial cultures are diluted to about $10^4$/ml in LB medium containing 1% DMSO. 0.5 ml of the suspension is distributed to each well of a 48-well microtiter plate. The compound is added to the wells to achieve 200, 100, 50, 25, 12.5, 6.25, 3.125, 1.575, or 0 micromolar concentrations of the compound. The plate is incubated for 24 hours at 37° C. and read by visual inspection of the wells. The minimal inhibitory concentration (MIC) is defined as the lowest concentration of inhibitor at which bacterial growth was not visually apparent.

Alternatively, MIC can be determined as follows. Stock solutions of the compound is added to individual containers of liquid LB media containing 1.4% agar at 60° C. to achieve compound concentrations of 48, 24, 12, 6, 3, 1.5, 0.75, 0.375, and 0.19 µg/ml. The LB agar is poured onto petri plates and solidified. 100 µl of about 500 to 1000 cfu is plated onto each petri plate, including a control plate without compound. The plates are incubated at 37° C. for 24 hours. MIC is determined as the lowest concentration at which no colony formation is observed.

E) In Vitro Cytotoxicity Screening

A candidate antimicrobial compound also can be screened for in vitro cytotoxicity. At various concentrations, the compound is added to small spinner cultures of exponentially growing mammalian cells (e.g., HeLa S3). At 8 hour intervals for the next 48 hours, samples are taken from the cultures and the cell number counted by standard, techniques (e.g., Coulter counting). Preferably, the compound is assessed at 3× and 10× the MIC concentration (see above).

F) In Vivo Lethal Protection Screening

To determine if a candidate antimicrobial compound can protect an animal from a lethal bacterial challenge, 20-gram female Swiss-Webster mice are infected with a single intraperitoneal (ip.) injection of methicillin-sensitive *S. aureus* "Smith" strain (0.5 ml in physiological saline; $4 \times 10^7$ cfu/mouse). One hour later, the mice are individually injected with various solutions/suspensions. The negative control mouse receives 0.1 ml of physiological saline. The positive control mouse receives 0.1 ml of a 4 mg/ml solution of vancomycin in saline, which corresponds to a dose of 20 mg/kg body weight. The test mouse receives about 1 to 10 mg/kg of the compound in an appropriate diluent. If the compound diluent is not saline, then another mouse is injected with the compound diluent as a second negative control. Each mouse is monitored for survival over a three day period. The compound is said to protect against this lethal challenge if the mouse injected with the compound lives or vancomycin lives, but the mouse receiving the diluent dies at the end of the observation period.

The protection screening can be performed by a commercial subcontractor, e.g., MDS Panlabs, Inc.

G) In Vivo Acute Toxicity Screening

The in vivo acute toxicity of a candidate antimicrobial compound can be determined. Various concentrations of the compound are administered to the tail vein of mice. Each mice receives 0.05 to 0.2 ml inoculum containing 25, 50, 100, or 150 mg compound/kg body weight. The mice are observed closely for 12 hours for signs of acute toxicity, such as lethargy, shivering, tendency to immobility, or hunchbacking. Doses which cause more than temporary discomfort are noted. All animals used in the study are euthanized by decapitation at the end of the observation period.

H) In Vivo Half Life

The intravenous in vivo half life of a candidate antimicrobial compound can be estimated. Mice are injected, via the tail vein, :with the highest dose that does not cause acute toxicity (see above). At 10, 20, 30, 45, 90, and 150 minutes after injection, two mice are decapitated and their blood collected by exsanguination into a sterile test tube. The blood samples are centrifuged, and the plasma collected. 0.2 ml of the plasma is used for HPLC analysis to determine the amount of compound in the blood at the indicated time after injection.

The half-life is determined by noting the time required for the blood compound level to reach 50% of any previously amount noted for a specific time, with the proviso that time points are taken during the decay phase of the blood compound levels. In other words, the maximum blood compound level is achieved before any timed sample is taken for the purpose of determining the half-life.

Alternatively, other tissues besides blood can be evaluated for compound levels after administration. For example, instead of collecting the blood from sacrificed mice, the liver can be collected, homogenized, cleared, and assayed for compound levels. The compound levels and half-lives in various tissues are useful for determining the tissue distribution of the compound and any variances between the blood compound levels and levels in other tissues under one method of administration.

Such results are also important in determining any pharmacological differences associated with a specific route of administration. For example, the compound could have a dramatically higher bioavailability in the lung when administered by inhalation than when administered subcutaneously.

I) In Vivo Efficacy Screening Using the Thigh Infection Mouse Model

In vivo efficacy screening also can be performed using the thigh infection model described below. This model is rational, flexible, relatively inexpensive, and reproducible. It is also well described in the art (see, e.g., Gudmundsson et al., *J. Antimicrob. Chemother.*, 31:177–191, 1993).

In the thigh infection mouse model, mice are made neutropenic (e.g., by administering cyclophosphamide to the mice) to render them susceptible to infection with a wide variety of bacteria. The mice are then infected by intramuscular (im). injection of test bacteria (one or more species) into the thigh. The infected mice are typically divided into at least three groups., The first group receives treatment with the candidate antimicrobial compound. A second group receives a known efficacious antibiotic (e.g., vancomycin). The third group receives only the diluent used to deliver the compound and antibiotic, if the diluent is the same in both cases. If the diluents used for the compound differs from that used for the vancomycin, another control group may be necessary to test the effect of the second diluent.

Just before the treatment begins, and at predetermined times after infection, animals are sacrificed. The portion of the thigh into which the bacteria had been injected is removed, homogenized in sterile saline, diluted, and plated onto standard bacterial agar plates to determine the bacterial content in cfu/ml.

Typically, the infection is designed to avoid death of untreated animals in the period of experimental observation. Death can be avoided if the inoculum and the period of observation are chosen such that the number of bacteria in the thigh of an untreated, infected animal increases by no more than two to three logs. The efficacy of the compound is typically based on the capacity of a given dose to prevent this increase and to reduce the bacterial load to lower than 50% of the load which is present in the diluent-treated animal. In this assay, 40 mg/kg vancomycin given intravenously every four hours produces a range of two to four log reduction in S. aureus proliferation compared with control thighs.

The choice of diluents and route of administration will be dictated primarily by the physiochemical properties of each candidate compound. For compounds that have significant solubility in water, dissolution and administrating in saline by any route is possible. More hydrophobic compounds may require a diluent of a mixture of DMSO and water (e.g., 80% DMSO [v/v]), or alternatively 90% peanut oil in DMSO for intraperitoneal administration. For subcutaneous administration, poorly soluble compounds can be micronized/solubilized in a mixture of glycerol, propylene glycol, and water.

IV. Pharmaceutical Compositions and Their Administration

The antimicrobial compounds of the invention can be formulated into pharmaceutical compositions suitable for administration into animals, especially humans.

A) New Antimicrobial Compounds

The new antimicrobial compounds typically contain three components: a Gram-positive eubacterial or mycoplasmal DNA polymerase III active site-binding moiety ("A"), a zinc finger-reactive moiety ("B"), and a linker ("L") which joins the pol III active site-binding moiety and the zinc finger-reactive moiety together. The new antimicrobial compound is represented by a general formula: A—(L—B)$_m$. As the novel antimicrobial compounds can contain up to 2 zinc finger-reactive moieties, m can be a positive integer 1 or 2.

The pol III active site-binding moiety can be modified from a compound known to bind to such an active site, e.g., one of the HPUra-like compounds having a formula as shown below:

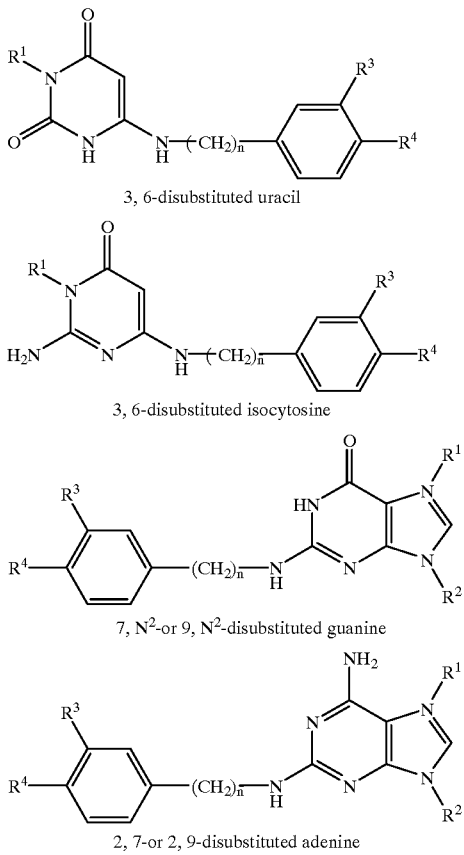

3, 6-disubstituted uracil 3, 6-disubstituted isocytosine

7, $N^2$-or 9, $N^2$-disubstituted guanine 2, 7-or 2, 9-disubstituted adenine

Each of $R^1$ and $R^2$, independently, is hydrogen, $C_{1-3}$ alkyl, $C_{1-3}$ haloalkyl, or —L—B. Each of $R^3$ and $R^4$, independently, is hydrogen, $C_{1-3}$ alkyl, halo, $C_{1-3}$ haloalkyl, or —L—B; and n is 0, 1, or 2; provided that at least one of $R^1$, $R^2$, $R^3$, and $R^4$, is —L—B.

The linker can be as short as a direct bond or as long as a $C_{18}$ alkylene chain. When the linker is an alkylene chain, it can optionally contain ether, thioether, amine, ester, thioester, or amide. For instance, the alkylene chain can contain multiple (e.g., 1–5) amine groups. A suitable example would be a —$(CH_2)_2$—NH—$(CH_2)_3$—NH—$(CH_2)_2$— group. The linker can also be a branched alkylene chain, e.g., a —CH(—$(CH_2)_3$—)—O—$(CH_2)_3$—O—$(CH_2)_2$— group, which can be attached to more than one zinc finger-reactive moiety. The ether, thioether, amine, ester, thioester, or amide group can also be present at the ends of the linker, thus joining the other two moieties to the linker.

The zinc finger-reactive moiety can be modified from a zinc finger-reactive group well known in the art, e.g., an azodi(bis)urea group, an aromatic or aliphatic disulfide group, an aromatic or aliphatic nitroso group, a thiosulfonate group, or a thiazolidone group. Such moieties eject or otherwise interact with the zinc ion from the zinc finger by either forming bonds with the zinc ion directly or bonding with the amino acid residues, e.g., cysteine or histidine residues, that coordinate with the zinc ion. Note that the word "bond" here can be any form of linkage such as a covalent bond, an ionic bond, or a hydrogen bond. See, e.g., Rice et al., *J. Med. Chem.*, 39:3606–3616 (1996); Otsuka et al., *J. Med. Chem.*, 37:4267–4269 (1994); Otsuka et al., *J. Med. Chem.*, 38:3264–3270 (1995); Fujita et al., *J. Med. Chem.*, 39:503–507 (1996); Loo et al., *J. Med. Chem.*, 39:4313–4320 (1996); Jaffe et al., *J. Biol. Chem.*, 259:5032–5036 (1984); and Louie et al., *Proc. Natl. Acad. Sci. USA*, 95:6663–6668 (1998).

A novel antimicrobial compound can be prepared by following the general procedure as set forth below.

B) Methods of Preparing New Antimicrobial Compounds

There exist many different routes for the preparation of the new antimicrobial compounds. The following general procedure is not limiting.

Preparation of the new antimicrobial compounds can begin with coupling a pol III active site-binding moiety ("A") to a linker ("L"). Methods of preparing 3-substituted pyrimidines and 7- and 9-substituted purines are described in detail in U.S. Pat. Nos. 5,516,905 and 5,646,155, respectively. The substituents can be further modified to form a linker moiety containing a functional group at its terminus for coupling to the zinc finger-reactive moiety ("B"). Suitable linker terminal functional groups include typical leaving groups for substitution reactions, e.g., halides; amine groups for forming amide linkages with activated carboxylic acid derivatives, e.g., acid halides; or thio groups for forming disulfide linkages with other thio-containing compounds. The following schemes exemplify the preparation of various novel antimicrobial compounds.

Preparation of L—A with a Suitable Terminal Functional Group for Coupling to B As described above, the moiety L can be modified to form a functional group for coupling to B. Three examples of such a functional group are illustrated below, i.e., —I (compound I), —SH (compound II), and —NH (compound III).

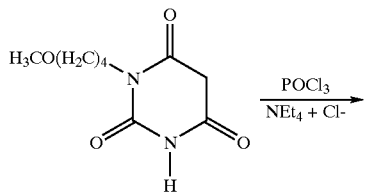

-continued

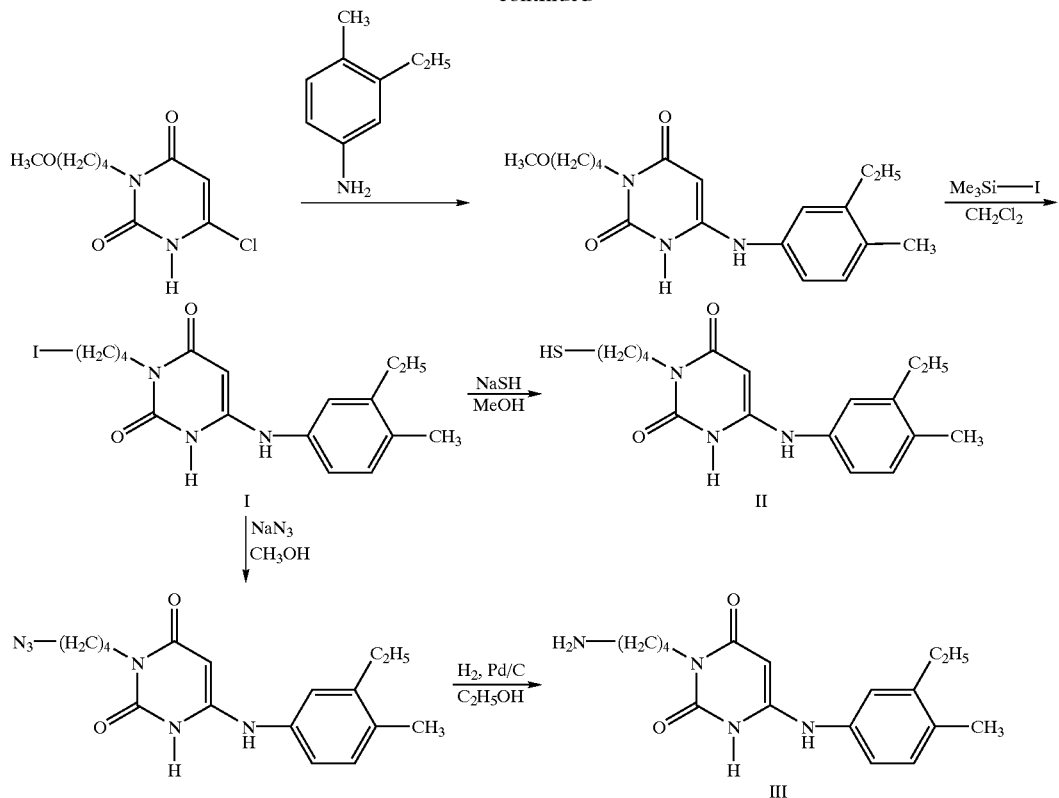

Coupling of L—A to B

The functional group on the moiety L can then be coupled e.g., by a coupling reaction such as alkylation, with B to yield the new antimicrobial compound. Exemplary coupling reactions are described below.

Reaction A

In reaction A, compound I undergoes a nucleophilic substitution to effect an amine linkage between A–L and B, and displaces the iodide as a leaving group.

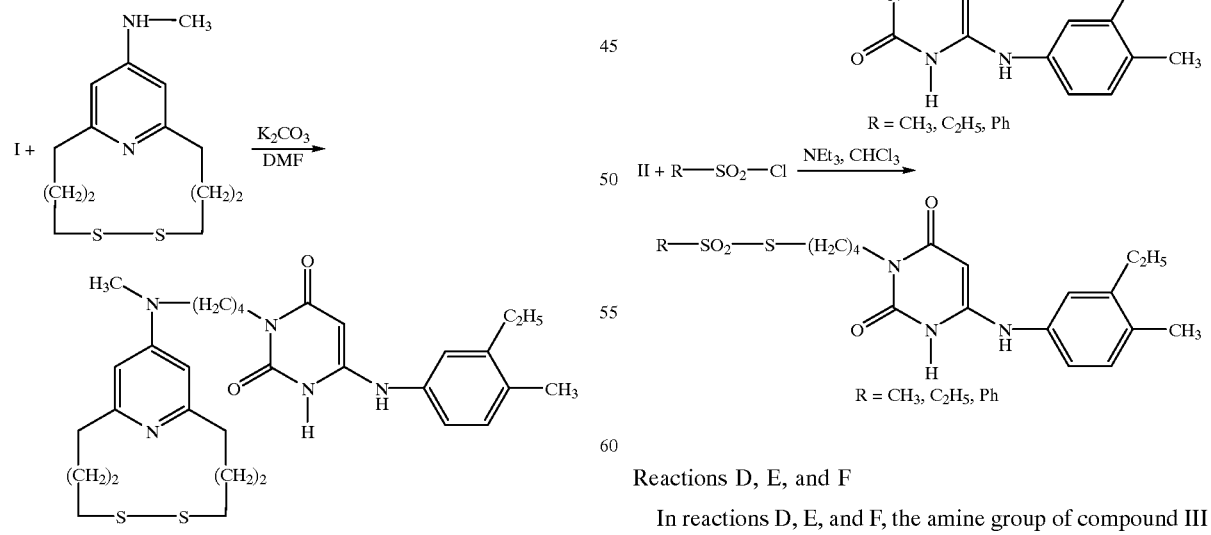

Reaction B

In reaction B, the thiol group of compound II displaces the methylsulfonyl group to form a disulfide linkage in the final antimicrobial compound. Similarly, a sulfonatethio linkage forms in the product as the chloride is displaced by the thiol group of compound II in reaction C.

Reactions D, E, and F

In reactions D, E, and F, the amine group of compound III reacts with an acid chloride, thereby forming an amide linkage. The nitrogen atom of the amide in reaction E further attacks the disulfide bond of moiety B and results in a formation of a ring.

Reaction D

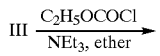

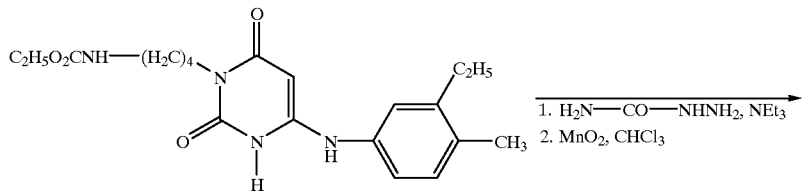

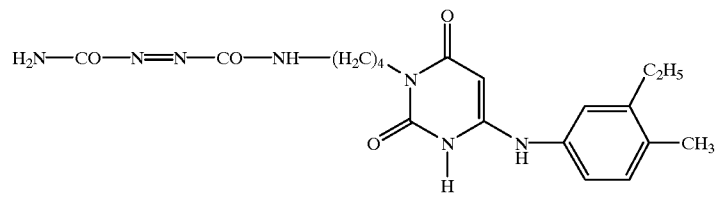

Reaction E

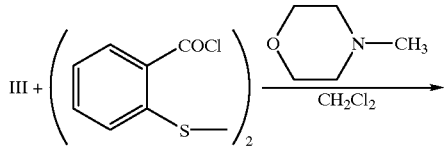

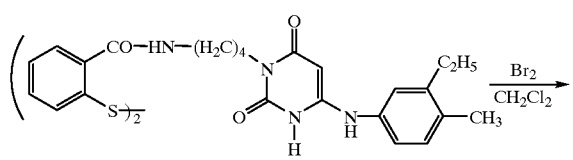

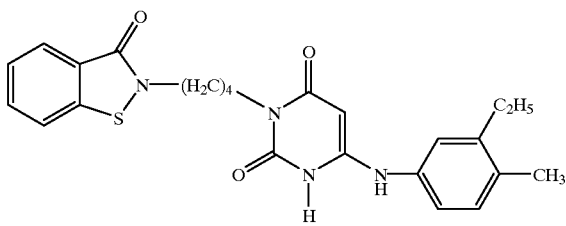

Reaction F

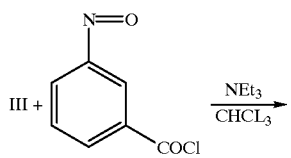

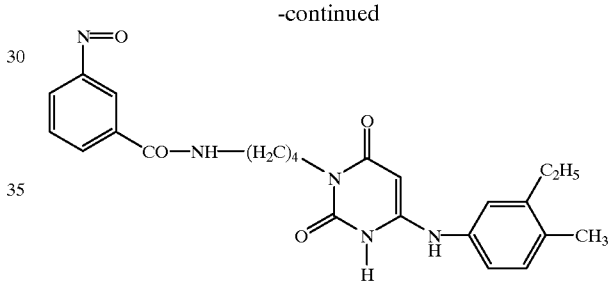

-continued

C) Formulation

The compositions can be formulated as a solution, suspension, suppository, tablet, granules, powder, capsules, ointment, or cream. In the preparation of these compositions, at least one pharmaceutical carrier can be included. Examples of pharmaceutical carriers include solvent (e.g., water or physiological saline), solubilizing agent (e.g., ethanol, polysorbates, or Cremophor EL®), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils) can be added. If necessary, glycerin, dimethylacetamide, 70% sodium lactate, a surfactant, or a basic substance such as sodium hydroxide, ethylenediamine, ethanolamine, sodium bicarbonate, arginine, meglumine, or trisaminomethane is added. Biodegradable polymers such as poly-D,L-lactide-co-glycolide or polyglycolide can be used as a bulk matrix if slow release of the composition is desired (see e.g., U.S.

Pat. Nos. 5,417,986, 4,675,381, and 4,450,150). Pharmaceutical preparations such as solutions, tablets, granules or capsules can be formed with these components. If the composition is administered orally, flavorings and colors can be added.

The concentration of the compound in the compositions of the invention will vary depending upon a number of factors, including the dosage to be administered, and the route of administration.

D) Administration

The compounds and compositions of the invention can be administered by parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol., scarification, and also oral, buccal, rectal, vaginal, or topical administration. The compositions of the invention may also be administered by the use of surgical implants which release the compounds of the invention.

In general terms, the compounds of the invention can be provided in an aqueous physiological buffer solution containing about 0.1 to 10% w/v compound for parenteral administration, typically after determining whether the patient is susceptible to or having a Gram-positive eubacterial or mycoplasmal infection. General dose ranges are from about 0.01 mg/kg to about 1 g/kg of body weight per day; a preferred dose range is from about 5 mg/kg to 100 mg/kg of body weight per day. The preferred dosage to be administered will depend upon the type and extent of progression of the infection being addressed, the overall health of the patient, and the route of administration. For. topical and oral administration, formulations and dosages can be similar to those used for other antibiotic drugs, e.g., erythromycin or vancomycin.

EXAMPLES

The invention will be further described in the following examples, which do not limit the scope of the invention defined in the claims.

Example 1

Each Molecule of a Gram-Positive Eubacterial Pol III Contains One Molecule of Zinc A highly conserved amino acid sequence in the N-terminal portion of the polymerase active site (pol) had of Gram-Positive Eubacterial DMA polymerase III the potential to form a zinc finger structure. Alignment of sequences from this region of various Gram-positive eubacterial pol IIIs (*Bacillus subtilis, Staphylococcus aureus, Clostridium acetobutyricum, Streptococcus pyogenes, Streptococcus pneumoniae, Enterococcus faecalis,* and *Thermotoga maritima*) and various mycoplasma (*Mycoplasma pulmonis, Mycoplasma genitalium,* and *Mycoplasma pneumoniae*) indicated that the proposed zinc fingers include either four cysteines (residues 1, 4, 2, 9 and 32 of SEQ ID NO:2) for coordination of the zinc ion, or one histidine and three cysreines (residues 1, 4, 2, 9 and 32 Of SEQ ID:2). Based on the above sequence analysis, an attempt was made to verify that a zinc ion is tightly bound to a zinc finger of a DNA polymerase.

Zinc finger structures typically bind a single atom of zinc with an affinity constant exceeding that of a zinc:EDTA complex. Therefore, the presence of strongly bound (EDTA-resistant) zinc in *B. subtilis* pol III was examined.

Two forms of the pol III were examined. One, the so-called wild-type pol III, was identical to the native enzyme found in *B. subtilis*. The other form incorporated a hexahistidine affinity tag at its N-terminus to facilitate its purification.

Both forms of *B. subtilis* pol III were generated in *E. coli* by inducible expression of the *B. subtilis* polC gene from recombinant plasmid vectors. Two different plasmid systems were used for expression. One, based in the plasmid pKC30 and *E. coli* AR120, has been described in Hammond et al., *Prot. Express. Purif.,* 3:65–70, 1992. The other system was based on plasmid pSGA04, an expression plasmid designed to generate recombinant proteins with a removable N-terminal hexahistidine tag (Ghosh et al., *Gene,* 176:249–255, 1996). Engineering of the polC sequence into pSGA04 required the following steps: (1) introduction, with PCR, of a new HpaI restriction site at nucleotide 16 of a form of polc which had been engineered previously to contain an XhoI site at position 1246 (Barnes et al., Gene, 165:45–50, 1995); (2) excision of the resulting 1228 bp HpaI-XhoI fragment; (3) recloning of the latter fragment into a fully wild-type polC construct in the vector pKC30 (Hammond et al., *Prot. Express. Purif.,* 3:65–70, 1992); (4) excision of the polC gene lacking the first 15 bases as a HpaI-BamHI fragment; and (5) insertion of the latter fragment into EcoRI-digested pSGA04 which had the sticky ends filled in by treatment with Klenow and subsequently digested with BamHI. This recombinant polC vector encoded and expressed a form of *B. subtilis* pol III in which the first six amino acids were replaced with the following 19-residue sequence: $NH_2$-M G H($_6$) S G <u>L F K R</u> H M S R I (SEQ ID NO:4). The underlined amino acids denote the cleavage site for protease Kex-2.

Both of the above plasmids were used to transform bacteria. Bacteria were grown in LB expression medium (0.5% yeast extract, 1% tryptone, 0.5% NaCl, and 0.15 mg/ml ampicillin).

Wild-type *B. subtilis* pol III was expressed from the pKC30 polc plasmid transformed into *E. coli* AR120. Induction of expression and purification of homogeneous enzyme were performed as described in Hammond et al., supra.

pSGA04 was introduced into *E. coli* SG101 (Ghosh et al., supra) by transformation. Individual transformants were grown at 30° C. to an absorbance (600 nm, 1 cm path length) of about 1.0 in LB expression medium containing 15 µg/ml kanamycin. The culture was then chilled to about 18° C., IPTG added to 1 mM, and incubation continued for about 18 hours at 18° C. with shaking. The cells were chilled to 0° C., centrifuged, washed once in phosphate-buffered saline (0.15 M NaCl and 50 mM potassium phosphate [pH 7.6]) containing 1 mM PMSF, and resuspended at 30 ml buffer (50 mM potassium phosphate; [pH 7.5], 2 mM β-mercaptoethanol, 20% glycerol, and 1 mM PMSF) for each one liter of culture.

Purification of hexahistidine-tagged pol III from one liter of induced culture was performed at 4° C. Cells were fractured in a French press and centrifuged at about 27,000×g for two hours. The resulting crude supernatant was loaded on a 12.5 ml column of $Ni^{+2}$-charged IMAC-agarose (Sigma; prepared according to manufacturer's instructions) equilibrated with IMAC column buffer (50 mM potassium phosphate [pH 7.5], 2 mM β-mercaptoethanol, and 20% glycerol). The column was washed with two volumes of IMAC column buffer, and eluted in a 0–200 mM imidazole gradient in the same buffer but containing 10% glycerol (total gradient volume of 250 ml). Fractions were collected and assayed for polymerase activity, and the peak fractions were pooled.

Polymerase activity was determined as described in Barnes et al., *Meth. Enzymol.*, 262:35–42, 1995, using activated calf thymus DNA (Worthington) as template and primer and [$^3$H]dTTP as the substrate. One unit of polymerase activity was defined as the activity which catalyzes the incorporation of one nanomole of [$^3$H]dTMP in 10 minutes at 30° C. For determination of the $K_M$ of the polymerase for DNA, the concentration of activated calf thymus DNA was varied during assay from 0–0.8 mg/ml. For determination of the $K_M$ for dGTP, incorporation of [$^3$H] dTMP was followed as a function of dGTP concentration (0–0.5 mM), and the values for incorporation were corrected for dGTP-independent, background incorporation.

Exonuclease activity was assayed as described in Barnes et al., supra, using single-stranded calf thymus DNA labeled at its 3' end with [$^3$H]dTMP as the substrate. One unit of exonuclease activity was defined as the activity which catalyzes the release of one nanomole of total nucleotide in 10 minutes at 30° C. For determination of the $K_M$ of the polymerase for the substrate, the concentration of single-stranded DNA was varied from 0–0.2 mg/ml.

The pooled IMAC fractions were loaded on a 20 ml MonoQ FPLC column (Pharmacia), washed with 60 ml of a buffer (50 mM potassium phosphate [pH 7.5], 5 mM β-mercaptoethanol, 10% glycerol), and eluted with a 0.1–0.6 M NaCl gradient in the same buffer. The total gradient volume was 240 ml. Two-milliliter fractions were collected and assayed for DNA polymerase activity as described above. Homogeneous peak fractions were pooled and used for subsequent analyses. With respect to its specific activity, its $K_M$ for activated DNA and dNTPs, and its affinity for the inhibitory dGTP analog TMAU, the tagged pol III is indistinguishable from the wild-type pol III expressed from pKC30. This result indicated that the N-terminal modification to pol III did not affect pol III function. Thus, the N-terminal tag segment was not removed from any of the tagged pol III prior to their use in experiments.

Each form of the protein was purified to greater than 95% homogeneity and reduced in volume to reach a concentration of 30–50 μm using a Filtron 10K. Both the wild-type and tagged forms of pol III retained greater than 80% of their original polymerase and exonuclease activities after concentration.

It was known that large proteins, particularly those with a high cysteine content, could strongly bind zinc and other trace metals non-specifically (Cornell et al., *Anal. Biochem.*, 47:203–208, 1972). To remove this non-specifically bound zinc, each pol III preparation was subjected to extensive dialysis against an EDTA dialysis buffer (100 mM NaCl, 10 mM β-mercaptoethanol, 10 mM EDTA, and 10 mM HEPES [pH 7.5]). All dialysis procedures were carried out at 0° C. and used metal-free plasticware, metal-depleted dialysis tubing, and procedures routinely employed in preparation of metalloproteins for metal analysis (Valle et al., *Physiol. Rev.*, 73:79–118, 1993).

Purified pol III was adjusted to a concentration of 0.5–5 μM with dialysis buffer and dialyzed against 100 volumes of dialysis buffer for 12 hours. This regimen was repeated five times using dialysis buffer, and a sixth time using dialysis buffer containing 0.01 mM β-mercaptoethanol but no EDTA. The samples were then concentrated by centrifugation in zinc-free concentrators (Filtron 10K) to yield solutions containing 20–30 μM enzyme. Both the wild-type and tagged pol III enzymes routinely retain greater than 80% of their original polymerase and exonuclease activity following this regimen of dialysis and concentration.

The stoichiometric zinc content of *B. subtilis* pol III was determined by subjecting 10–60 μM solutions of EDTA-dialysed pol III to atomic absorption spectroscopy using a Perkin-Elmer 2280 flame instrument. All measurements incorporated the determination and subtraction of the metal content of appropriate dialysate controls.

Five independently-derived samples of pol III were analyzed. Four of the wild-type form and one of tagged form. Prior to EDTA treatment, each of the five samples contained greater than four atoms of zinc per mole of protein, a level not unexpected for a large, undialyzed protein rich in zinc-scavenging thiol groups (*B. subtilis* pol III contains 15 cysteine residues). The five-day regimen of dialysis against 10 mM EDTA removed this non-specifically bound zinc from the enzyme, reducing the zinc content to a level which was not diminished further by extending the period of dialysis for up to three more days.

The respective values for the EDTA-resistant zinc content obtained after this exhaustive regimen of dialysis of the four dialyzed pol III samples and the one tagged pol III were 1.2, 1.2, 1.0, 0.8, and 1.1 gram-atoms per mole protein, respectively. These values strongly suggested that zinc was tightly bound to the pol III in a stoichiometry equal to one atom per molecule of pol III.

Example 2

Pol III Zinc is Ejected by the Electroihile MMTS

The presence of a single, EDTA-resistant zinc atom in the *B. subtilis* pol III was consistent with its coordination in one of the two zinc finger structures as described above. Since the zinc in both of these hypothetical zinc fingers was coordinated with cysteine, the susceptibility of the zinc finger to methylmethanethio-sulfonate (MMTS) modification was examined. MMTS is a thiol-specific reagent which had been widely used to eject zinc from accessible cysteine-based zinc fingers (Smith et al., *Biochem.*, 14:766–771, 1975 and Jaffe et al., *J. Biol. Chem.*, 259:5032–5036, 1984). MMTS is a strong electrophile which ejects the zinc by converting the coordinating thiolate of a cysteine to its respective methyl disulfide, forming the structure, $CH_3$—S—S—$CH_2$-PROTEIN, thereby destroying the zinc finger's capacity to coordinate zinc.

Pol III was labeled by growing bacteria transformed with the above-described pol III expression plasmids in the presence of $^{65}$Zn. LB expression medium was first depleted of divalent trace metals by mixing the medium with 0.3 volume of Chelex-Na (Bio-Rad) for 24 hours at 0° C. The depleted medium was then supplemented with 0.1 mM $MgCl_2$ to support a level of *E. coli* growth compatible with pol III expression. *E. coli* AR120 transformed with the pKC30/polC vector was grown at 30° C. in this magnesium-supplemented medium. When the culture reached an absorbance of 0.5 (600 nM, 1 cm path length), 10 ml of the culture was added to one liter of the zinc-depleted, magnesium-supplemented medium, which further included [$^{65}$Zn]$Cl_2$ (New England Nuclear; specific activity of 2.7 mCi/μmole) to a radioactivity level of 1.1 μCi/ml medium. Incubation was continued until the culture reached an absorbance of 0.75. The culture was then induced and pol III prepared as described in Example 1 above.

To remove non-specifically bound $^{65}$Zn and exogenous thiols, the pol III was dialyzed as described in Example 1 above, and the labeled protein was further dialyzed with HNE buffer (10 mM HEPES [pH 7.6], 100 mM NaCl, and 0.1 mM EDTA) to remove exogenous thiols. The protein concentration was adjusted to about 1 μm in HNE buffer. 100 μl samples having about 25,000 counts per minute per sample were incubated at 0° C. in the absence or presence of MMTS at 0.01, 0.03, 0.10, or 0.3 mM. After 60 minutes, each mixture was applied to a calibrated Sephadex G-25 column capable of separating protein from free $ZnCl_2$ (1.0 ml bed volume, 0.38 ml void volume; equilibrated with HNE buffer). The column was eluted in 0.05 ml steps. The fraction eluted with each step was analyzed by liquid scintillation counting to determine the amount of protein-bound $^{65}Zn$ (void volume) and the amount of free $^{65}Zn$ (included volume).

In the absence of MMTS, all of the $^{65}Zn$ radioactivity remained bound to the protein as expected. In the presence of 0.01 mM MMTS, about 50% of the label was released. At the three higher concentrations release was essentially complete (greater than 95%). These results suggested that the zinc ion was tightly coordinated with pol III cysteines, consistent with the hypothesis that the zinc was bound by the pol III zinc finger.

Example 3

Pol III Zinc is Replaceable by Iron or Cobalt

It was known that tetrahedrally coordinated zinc in zinc finger structures frequently accommodate metal ions other than $Zn^{+2}$ (Valle et al., *Proteins*, 5:94–128, 1970). To determine whether the zinc binding site of *B. subtilis* pol III shared this property, the ability to replace the pol III zinc with an iron atom was examined.

An indirect approach based on expression of the recombinant pol III in medium specifically enriched for iron was used for the replacement procedure. Exploiting the trace metal-deficient medium that was used to generated the $^{65}Zn$-labeled enzyme in Example 2 above, pol III was produced in the absence of added metal and in the presence of the respective chloride salts of $Zn^{+2}$, $CO^{+2}$, and $Fe^{+2}$, each at a concentration of 0.1 mM. The cells from the respective cultures were harvested, and their crude extracts were prepared and analyzed to determine the specific activity of pol III.

The specific polymerase activity of each extract was determined and normalized to the specific activity of an identical control extract of cells which were induced to express pol III in conventional LB expression medium. Without any metal supplementation, the normalized specific activity was 0.2. With the addition of zinc, the specific activity was 1.1, similar to the control as expected. Supplementation with iron or cobalt resulted in specific activities of 1.2 and 1.0, respectively, indicating that both iron and cobalt can functionally substitute for the zinc bound to pol III.

SDS-PAGE analysis of the above extracts indicated that the zinc-, iron-, and cobalt-supplemented cultures produced levels of the 160 kD *B. subtilis* pol III polypeptide equivalent to that of control cultures. Thus, the observed differences and similarities in specific activities cannot be due to differences in protein expression levels.

The iron-substituted pol III was further characterized. This enzyme behaved identically to the control enzyme in terms of purification profile, polymerase activity, exonuclease activity, substrate affinity, sensitivity to TMAU, and stability during EDTA dialysis. Atomic absorption spectrometric analysis (see Example 1 for procedure) of a single sample of a homogeneous, EDTA-dialysed iron-pol III indicated an iron content of 1.05 gram-atoms per mole protein and a zinc content of less than 0.2 gram-atom per mole protein. This result indicated that the pol III zinc binding site had an architecture consistent with that of the proposed zinc finger structures for pol III as described aboved.

Example 4

Removal of Zinc from Pol III Abolishes Polymerase Activity

As discussed in Example 3, production of *B. subtilis* pol III in a zinc-free medium resulted in a substantially crippled enzyme having 20% of the polymerase activity of native pol III. To confirm the functional necessity of zinc for optimal pol III activity, the effect of directly removing zinc from pol III was examined.

Removal of zinc by treatment with a chelating compound. A number of strong metal chelators have been synthesized and tested for their zinc finger-disruption activity (Otsuka et al., *J. Med. Chem.*, 38:3264–3270, 1995). One related chelator, Compound 20 as described in Otsuka et al.,*J. Med. Chem.*, 39:503–507 (1996), was used in the following experiment, which exploited homogeneous *B. subtilis* pol III labeled with radioactive $^{65}Zn$. An identical control experiment was performed in the absence of Compound 20.

0.2 nanomoles of pol III was mixed in 0.1 ml of HNE buffer (10 mM HEPES, 100 mM NaCl, and 10% glycerol [pH 7.6]) containing 0.3 mM Compound 20, and the mixture was incubated at 25° C. for one hour. The pol III was removed from Compound 20 by passage through a Sephadex G-25 spin column, and the enzyme assayed for polymerase activity and for its content of radioactive zinc (see procedures described above). The pol III sample incubated in the presence of Compound 20 displayed less than 1% of the control pol III activity and less than 2% of the radioactive zinc content of the control.

In an effort to reconstitute the zinc-deficient, inactive polymerase, the pol III was separated from Compound 20 as described above and incubated with 0.01 mM $ZnCl_2$, with or without 0.01 mM dithiothreitol (DTT), at 25° C. for 12 hours. At 30 minute intervals, samples were removed and assayed for pol activity. No reactivation of pol activity above the residual background was observed, nor was significant inactivation of polymerase activity observed for the untreated control pol III incubated with $ZnCl_2$, with or without DTT, under identical conditions.

Ejection of Zinc by Treatment of Coordinating Thiolates with MMTS. The compound MMTS is described in Example 2 above. 0.2 nanomoles of $^{65}Zn$-labeled *B. subtilis* pol III was incubated with HNE buffer with or without 0.2 mM MMTS for one hour, and the samples assayed as described for the pol III treatment with Compound 20. The pol III sample incubated in the presence of MMTS displayed less than 1% of the control pol III activity and less than 2% of the radioactive zinc content of the control pol III.

In an effort to reconstitute inactive polymerase, the enzyme was mixed with a solution containing 0.01 mM $ZnCl_2$ and 0.01 mM DTT and incubated for 25° C. for 12 hours. At 30 minute intervals, samples were removed and assayed for pol activity. No reactivation of pol activity above the residual background was observed, nor was significant inactivation of polymerase activity observed for the control pol III incubated with zinc and DTT under identical conditions.

The above results indicated that removal of zinc significantly inhibited (greater than 95% inhibition) the polymerase activity of a Gram-positive eubacterial pol III, and that such removal and enzymatic inactivation was irreversible.

Example 5

Site-Directed Mutagenesis of Critical Zinc Finger Residues Affects Pol III Activity To further confirm that one of the zinc finger structures proposed above was authentic, site-directed mutagenesis was used to mutate each of the proposed coordinating cysteines or the histidine to alanine.

An oligonucleotide-based system (Altered Sites, Promega) was used to introduce the mutations into the segment of polC encoding the putative zinc finger. The mutations were introduced into pZF-150, a subcloned fragment encompassing polC nucleotides 2410–2899 and bounded by the unique restriction sites SalI and ClaI, the former of which was created by site-directed mutagenesis. Each mutagenic oligonucleotide was designed such that the mutation simultaneously created a unique diagnostic restriction site within the targeted codon. The mutant forms of pZF-150 were recloned into the polc sequence, using the unique SalI and ClaI sites. The respective mutant polC constructs were then installed into the pSGA04 his6 expression plasmid by (1) recloning of the relevant SalI-ClaI fragment into SalI, ClaI-digested wild-type construct in the Bluescript plasmid (Stratagene); and (2) subcloning of the XhoI-ClaI Bluescript fragment into an XhoI, ClaI-digested pSGA04.

Each residue was mutated to alanine, replacing the zinc-coordinating thiolate side chains with a neutral methyl group. If any of these five coordinators were intimately involved in zinc coordination, its replacement with a methyl group would be expected to significantly weaken, if not effectively destroy, the affinity of the enzyme for zinc.

Tagged wild-type and mutant forms of pol III were obtained at greater than 95% homogeneity using the procedure of Example 1 above. The proteins were then subjected to EDTA-based dialysis, and analyzed for zinc content as described in Example 1. The results are summarized in the left-most column of Table I, below.

finger. In any event, the truncated protein was not considered a legitimate candidate for comparison with the full-length proteins.

Each of the three full-length mutants (C912A, C915A, and C940A) displayed reduced affinity for zinc (zinc content) relative to the wild-type enzyme. The C915A protein was closest to the wild-type protein in affinity, retaining approximately 40% of the zinc content of the wild-type enzyme. The C940A and C912A proteins were significantly more impaired, retaining only 10% and 7% of the wild-type zinc content, respectively.

Each of the five purified mutant enzymes of Table I was analyzed directly, in its native, undialyzed form, to assess the impact of the respective mutation on (1) exonuclease and polymerase activity; (2) affinity for exonuclease and polymerase substrates; and (3) sensitivity of the polymerase activity to TMAU, a dGTP analog which inhibits the pol III of Gram-positive eubacteria (Wright et al., Pharmac. Therap., 47:447–497, 1990). The results are summarized in Table I.

Each mutation reduced both the exonuclease and polymerase activities. However, the reduction was significantly polymerase-specific, with the relative reduction of polymerase being much greater than the reduction of exonuclease activity in four relevant cases. The lowest exonuclease activity observed in a mutant was 20% of wild-type, while polymerase activity ranged from 10% to less than 0.1% of wild-type for the four full-length mutants legitimately comparable to wild-type enzyme.

None of the four mutant proteins assayed (including the truncated C937A protein) displayed an affinity for single-stranded substrate DNA which differed significantly from that of the wild-type enzyme. Nor did mutations C915A and C940A significantly affect dGTP substrate affinity and TMAU sensitivity. The $K_M$ for DNA and enzyme or dGTP and enzyme varied less than two-fold from wild-type values. $IC_{50}$ values for TMAU varied even less than two-fold.

These results did not help distinguish which of the zinc finger structures in proposed above was operative in the

TABLE I

| Enzyme | Zn Content (gm-atoms/mol) | Relative Specific Activity | | Substrate Affinity ($K_M$) | | TMAU Sensitivity (pol) |
| --- | --- | --- | --- | --- | --- | --- |
| | | Exo | Pol | Exo (mg/ml DNA) | Pol ($\mu$M dGTP) | ($IC_{50}$) |
| Wildtype | 1.1 | 1 | 1 | 0.033 | 0.065 | 1.8 | 4.1 $\mu$M |
| H909A | — | 0.3 | 0.01 | — | — | — | 4.0 $\mu$M |
| C912A | 0.07 | 0.3 | <0.001 | 0.027 | — | — | — |
| C915A | 0.4 | 0.2 | 0.06 | 0.021 | 0.086 | 1.9 | 2.9 $\mu$M |
| C937A* | — | 0.6 | nd | 0.024 | — | — | — |
| C940A | 0.1 | 0.4 | 0.1 | 0.032 | 0.115 | 0.8 | 4.0 $\mu$M |

The data for Table 1 were generated by the procedures describe in Example 1 above. "*" refers to the truncated protein missing the entire pol domain (i.e., aa 1000–1437). "nd" means not detectable. "- -" means that the parameter or value was not determined.

As noted in the Table 1, two of the five mutant enzymes, H909A and C937A, were not amenable to zinc analysis. The H909A enzyme, although expressed as a full-length protein, was not readily produced in an amount sufficient for metal analysis. The C937A enzyme purified as a truncated protein of 110 kD, also gave a poor yield. This truncated pol III was likely generated by interruption of translation within the zinc native protein. Nevertheless, the mutational analysis clearly established the critical role of these key residues in pol III function. Thus, the results are consistent with and support a zinc finger structure in Gram-positive eubacterial pol III.

Example 6

Preparation of 6-(meta-disulfidemethyl anilino) uracil 6-chlorouracil (1 mmol) and meta-aminobenzyl alcohol (2.0 mmol) were dissolved in 10 ml 2-methoxyethanol to form a reaction mixture. The mixture was then stirred at reflux for 10 hours to form 6-(meta-hydroxymethyl anilino)

uracil with a yield of 86%. The hydroxy group was displaced by a bromo group by reacting the hydroxymethyl anilino-uracil (0.5 mmol) with 30% HBr in acetic acid (10 ml), thus forming 6-(meta-bromomethyl anilino)uracil with a yield of 90%. The bromo group was further replaced by a thiocyanate group by reacting 0.4 mmol 6-(meta-bromomethyl anilino)uracil with 2 mmol KSCN to form 6-(meta-mercaptocyanomethyl anilino)uracil (MMCMAU) with a yield of 80%. mMCMAU was then hydrolyzed to 6-(meta-thiomethyl anilino)uracil in 5 mL of 2N NaOH. The final product, 6-(meta-disulfidemethyl anilino)uracil, was formed quantitatively by reacting 6-(meta-thiomethyl anilino)uracil with methyl methane thiosulfonate in 2 molar excess.

Example 7

Screening for Compounds That Remove Zinc from Pol III $^{65}$Zn-labeled *B. subtilis* pol III is produced and purified as described in Example 2. One hundred microliters of a 100 μg/ml solution of labeled pol III containing about 25,000 cpm of radioactivity is mixed with one microgram of a candidate antimicrobial compound at 25° C. for one hour. The mixture is then passed through a Sephadex G-25 spin column, and the eluate (protein) counted on a scintillation counter. The counts per minute of the eluate is compared to a control reaction where only the relevant control solvent is added to the mixture instead of the compound. The radioactivity released by the compound is greater than adding solvent alone to the reaction, indicating that the compound may be an effective antimicrobial.

To confirm the positive result, the procedure is repeated until a statistically significant determination can be made.

Example 8

Screening for Compounds that Inhibit Pol III Polymerase Activity

Five microliters of an appropriate dilution of *B. subtilis* pol III is rapidly mixed with 20 A$^1$ of polymerase assay mix (18.75 mM Tris [pH 7.5], 12.5 mM magnesium acetate, 31.25 μm DATP, 31.25 μm dCTP, 31.25 μm dGTP, 12.5 μm [methyl-$^3$H]dTTP [1.5 μCi/μmol], 1.25 mM DTT, 20% glycerol, and 0.5 mg/ml activated DNA) with or without the candidate antimicrobial compound, and incubated at 30° C. for 10 minutes. Reactions are stopped by addition of 0.5 ml cold 10% trichloroacetic acid (TCA) in 10 mM sodium pyrophosphate. After approximately 10 minutes at 0° C., samples are filtered on Whatman GF/A filters and washed, first with cold 1 M HCl in 100 mM sodium pyrophosphate, then with cold ethanol. Filters are dried and counted. If the presence of the candidate antimicrobial compound leads to at least a 25% inhibition in polymerase activity, the compound is deemed to be an inhibitor of polymerase activity.

The inhibitors which test positive in the screening assay immediately above is assessed for the capacity to inhibit bacterial DNA synthesis selectively (i.e., without significantly inhibiting bacterial RNA synthesis). Each inhibitor is assayed for its capacity to inhibit the incorporation of radioactively labeled adenine (a DNA and RNA base) into DNA and RNA in exponentially growing *B. subtilis* (Brown, *Proc. Natl. Acad. Sci. USA,* 67:1454–1460, 1970). In this assay, a candidate inhibitor is deemed DNA-selective if it can effect at least 50% inhibition of radioactive adenine incorporation into DNA and less than 15% inhibition of radioactive adenine incorporation into RNA.

Example 9

Screening for Bacteriocidal Compounds

The candidate antimicrobial compound is dissolved in sterile DMSO and diluted 100-fold into Mueller-Hinton broth (MHB; Difco) containing log-phase methicillin-sensitive *S. aureus* (ATCC No. 29213) at about 10$^6$ colony forming units (cfu) per milliliter. Only DMSO is added to the control culture. Compound and control cultures are incubated at 37° C., and samples from the cultures are removed every three hours during the next 24 hours. Each sample is assayed for the amount of bacteria (in cfu/ml) by diluting 10× and 100× in MHB and plating on LB agar plates. The candidate compound reduced the amount of bacteria by at least 50% for the six hour time point and thereafter, indicating that the compound is bacteriocidal.

Example 10

Screening for Compounds that Reduce Bacterial Infections In Vivo

Before infection with test bacteria, six six-week old pathogen-free ICR/Swiss mice are rendered neutropenic (less than 100 neutrophils per milliliter of blood) by intraperitoneal injection of two doses of cyclophosphamide. The first injection is made at 150 mg/kg four days before bacterial infection, and the second injection is made at 100 mg/kg one day before bacterial infection. Neutropenia is induced so that a wide variety of bacteria can be used for the subsequent infection.

Bacterial infection for each mouse is performed by inoculating 10$^6$ cfu of methicillin-sensitive *S. aureus* (ATCC No. 29213) in 100 μl of media into the right thigh muscle. The compound and control mixtures are administered intravenously into the tail vein of the animal at 2, 6, 12, and 18 hours post-infection. Two mice received 50 μl of a negative control mixture of physiological saline at each time point. Another pair of mice received a positive control mixture of 40 mg/kg body weight vancomycin in saline at each time point. The last two mice received 40 mg/kg body weight of the candidate compound in saline at each time point.

At 24 hours after infection, all mice are sacrificed, and the right thigh muscle of each mice removed. The muscle is then homogenized in 10 ml of chilled sterile saline in a Polytron tissue homogenizer. The 100× diluted homogenate is plated on LB agar plates. After incubating at 37° C. for 24 hours, the number of colonies on each plate is counted. Both muscle samples from the compound-treated mice yielded 50 colonies or less, whereas the muscle samples from the negative control animals (receiving saline only) yielded about 500 colonies on each plate. The muscle samples from the vancomycin-treated mice yielded about 40 colonies on each plate. Since the compound treatment leads to more than a 50% reduction in the amount of bacteria, the compound is said to be an effective antimicrobial.

OTHER EMBODIMENTS

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

What is claimed is:

1. A compound having the formula:

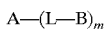

wherein

A is a polymerase III active site-binding moiety selected from the group consisting of:

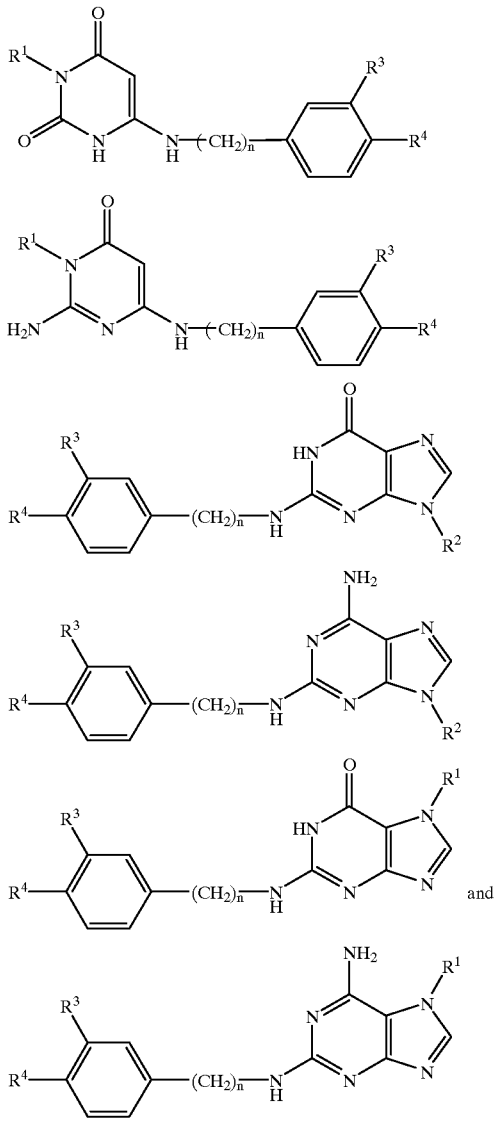

in which each of $R^1$ and $R^2$, independently, is hydrogen, $C_{1-3}$ alkyl, $C_{1-3}$ haloalkyl, or —L—B; each of $R^3$ and $R^4$, independently, is hydrogen, $C_{1-3}$ alkyl, halo, $C_{1-3}$ haloalkyl, or —L—B; m is 1 or 2; and n is 0, 1, or 2; provided that at least one of $R^1$, $R^2$, $R^3$, and $R^4$, is —L—B;

L is a linker; and

B is a zinc finger-reactive moiety selected from the group consisting of:

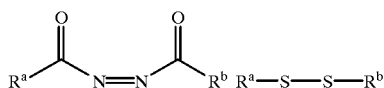

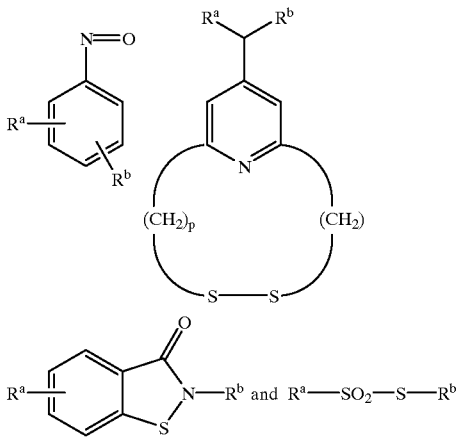

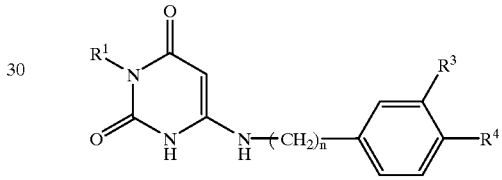

wherein each of $R^a$ and $R^b$, independently, is hydrogen, $C_{1-6}$ alkyl, phenyl, $C_{1-6}$ hydroxyalkyl, $C_{1-6}$ haloalkyl, amine, or —L—A; and p is 1, 2, 3, or 4; provided that either one of $R^a$ and $R^b$ is —L—A, and $R^a$ and $R^b$ are not —L—A simultaneously;

or a salt thereof.

2. The compound of claim 1, wherein A is of the formula:

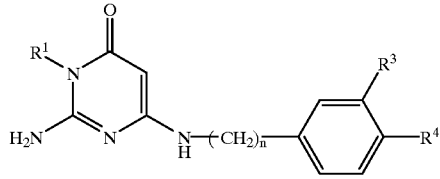

in which $R^1$ is hydrogen, $C_{1-3}$ alkyl, $C_{1-3}$ haloalkyl, or —L—B; each of $R^3$ and $R^4$, independently, is hydrogen, $C_{1-3}$ alkyl, halo, $C_{1-3}$ haloalkyl, or —L—B; and n is 0, 1, or 2; provided that at least one of $R^1$, $R^3$, and $R^4$, is —L—B;

or a salt thereof.

3. The compound of claim 1, wherein L is a direct bond or a $C_{1-8}$ alkylene chain; the alkylene chain optionally containing 1 to 5 —O—, —S—, —NR—, —C(=O)—O—, —C(=S)—O—, or —C(=O)—NR—; R being hydrogen or $C_{1-3}$ alkyl; or a salt thereof.

4. The compound of claim 2, wherein $R^1$ is —L—B.

5. The compound of claim 4, wherein $R^3$ is ethyl, halo, or $C_{1-3}$ haloalkyl and $R^4$ is methyl.

6. The compound of claim 1, wherein A is of the formula:

in which $R^1$ is hydrogen, $C_{1-3}$ alkyl, $C_{1-3}$ haloalkyl, or —L—B; each of $R^3$ and $R^4$, independently, is hydrogen, $C_{1-3}$ alkyl, halo, $C_{1-3}$ haloalkyl, or —L—B; and n is 0, 1, or 2; provided that at least one of $R^1$, $R^3$, and $R^4$, is —L—B;

or a salt thereof.

7. The compound of claim 6, wherein $R^1$ is —L—B.

8. The compound of claim 1, wherein $R^3$ is ethyl, halo, or $C_{1-3}$ haloalkyl and $R^4$ is methyl.

9. The compound of claim 1, wherein A is of the formula:

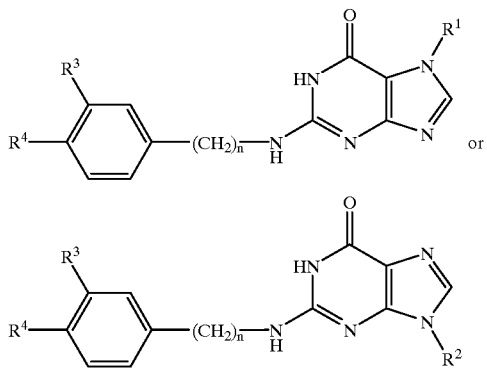

in which
each of $R^1$ and $R^2$, independently, is hydrogen, $C_{1-3}$ alkyl, $C_{1-3}$ haloalkyl, or —L—B; each of $R^3$ and $R^4$, independently, is hydrogen, $C_{1-3}$ alkyl, halo, $C_{1-3}$ haloalkyl, or —L—B; m is 1 or 2; and n is 0, 1, or 2; provided that at least one of $R^1$, $R^2$, $R^3$, and $R^4$, is —L—B;

or a salt thereof.

10. The compound of claim 9, wherein $R^1$ is —L—B.

11. The compound of claim 10, wherein $R^3$ is ethyl, halo, or $C_{1-3}$ haloalkyl and $R^4$ is methyl.

12. The compound of claim 9, wherein $R^2$ is —L—B.

13. The compound of claim 12, wherein $R^3$ is ethyl, halo, or $C_{1-3}$ haloalkyl and $R^4$ is methyl.

14. The compound of claim 1, wherein A is

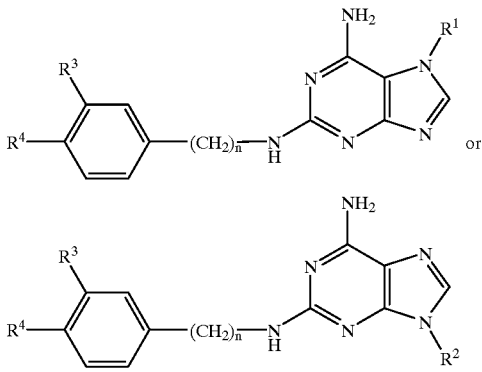

in which
each of $R^1$ and $R^2$, independently, is hydrogen, $C_{1-3}$ alkyl, $C_{1-3}$ haloalkyl, or —L—B; each of $R^3$ and $R^4$, independently, is hydrogen, $C_{1-3}$ alkyl, halo, $C_{1-3}$ haloalkyl, or —L—B; m is 1 or 2; and n is 0, 1, or 2; provided that at least one of $R^1$, $R^2$, $R^3$, and $R^4$, is —L—B;

or a salt thereof.

15. The compound of claim 14, wherein $R^1$ is —L—B.

16. The compound of claim 15, wherein $R^3$ is ethyl, halo, or $C_{1-3}$ haloalkyl and $R^4$ is methyl.

17. The compound of claim 14, wherein $R^2$ is —L—B.

18. The compound of claim 17, wherein $R^3$ is ethyl, halo, or $C_{1-3}$ haloalkyl and $R^4$ is methyl.

19. The compound of claim 1, wherein $R^3$ is ethyl, halo, or $C_{1-3}$ haloalkyl and $R^4$ is methyl.

* * * * *